United States Patent [19]
Babler et al.

[11] Patent Number: 5,690,892
[45] Date of Patent: Nov. 25, 1997

[54] CASSETTE FOR USE WITH AUTOMATED SPECIMEN HANDLING SYSTEM

[75] Inventors: Egan Babler, Northbrook; Richard A. Domanik, Libertyville; Peter G. Gombrich, Chicago; William J. Mayer, South Barrington, all of Ill.

[73] Assignee: AccuMed, Inc., Chicago, Ill.

[21] Appl. No.: 528,791

[22] Filed: Sep. 15, 1995

[51] Int. Cl.$^6$ .................................................. G01N 35/04
[52] U.S. Cl. .............................. 422/63; 422/65; 422/67; 422/102; 436/43; 436/47; 436/48
[58] Field of Search ........................... 422/63, 65, 67, 422/102, 104; 436/43, 44, 46, 47, 48; 206/456, 459.1, 569; 73/863.01, 864.91

[56] References Cited

U.S. PATENT DOCUMENTS

| | | | |
|---|---|---|---|
| 3,416,250 | 12/1968 | Schweers | 206/456 |
| 3,418,456 | 12/1968 | Hamisch et al. | 235/464 |
| 3,600,556 | 8/1971 | Acker | 235/464 |
| 3,745,314 | 7/1973 | Mathias et al. | 235/470 |
| 3,851,972 | 12/1974 | Smith et al. | 356/72 |
| 3,902,615 | 9/1975 | Levy et al. | 214/301 |
| 4,141,458 | 2/1979 | Brooks et al. | 214/301 |
| 4,142,863 | 3/1979 | Covington et al. | 422/63 |
| 4,250,405 | 2/1981 | Ashcroft et al. | 235/456 |
| 4,367,915 | 1/1983 | Georges | 350/530 |
| 4,402,613 | 9/1983 | Daly et al. | 356/446 |
| 4,427,332 | 1/1984 | Manriquez | 414/331 |
| 4,449,042 | 5/1984 | Hampson et al. | 235/464 |
| 4,588,341 | 5/1986 | Motoda | 414/32 |
| 4,658,960 | 4/1987 | Iwasa | 206/459 |
| 4,827,395 | 5/1989 | Anders et al. | 364/138 |
| 4,965,725 | 10/1990 | Rutenberg | 364/413.1 |
| 5,021,218 | 6/1991 | Davis et al. | 422/104 |
| 5,081,038 | 1/1992 | Sugaya et al. | 436/46 |
| 5,154,889 | 10/1992 | Muraishi | 422/65 |
| 5,209,903 | 5/1993 | Kanamori et al. | 422/65 |
| 5,245,530 | 9/1993 | Taki | 364/167.01 |
| 5,260,556 | 11/1993 | Lake et al. | 235/494 |
| 5,270,006 | 12/1993 | Uchigaki et al. | 422/63 |
| 5,287,182 | 2/1994 | Haskell et al. | 348/500 |
| 5,287,272 | 2/1994 | Rutenberg et al. | 364/413.01 |
| 5,332,549 | 7/1994 | MacIndoe, Jr. | 422/63 |
| 5,380,488 | 1/1995 | Wakatake | 422/65 |

FOREIGN PATENT DOCUMENTS

| | | |
|---|---|---|
| 849379 | 8/1970 | Canada. |
| 63-305510 | 12/1988 | Japan. |
| WO 90/07162 | 6/1990 | WIPO. |

OTHER PUBLICATIONS

"Nikon Biostation® Creates A Fully Automated Cytology Workstation In Your Laboratory", pp. 1-3, Feb. 1994.

G. Brugal et al., "Introduction to Cytometry and Histometry", pp. 1-7, dated Jan. 20-24 and 27-31, 1992.

Article entitled "Autostage System", p. 165, Photonics Spectra, Jun. 1994.

The LEP Robotic Slide Handling System (description and photograph), by Ludl Electronic Products Ltd., date unknown.

*Primary Examiner*—Harold Pyon
*Attorney, Agent, or Firm*—McDonnell Boehnen Hulbert & Berghoff

[57] ABSTRACT

A portable specimen transporting cassette for use with an automated specimen handling system The cassette includes a body portion, an electronic programmable memory device attached to the body portion, and an electrical conductor coupled to the memory device. The body portion includes right and left opposing sidewalls, and a substantially open front face between the opposing sidewalls. A plurality of ribs compartmentalize the body portion into superimposed sections, each capable of containing a specimen. The substantially open front face permits the specimens to be inserted into and withdrawn from the cassette. The electrical conductor interfaces with the specimen handling system and permits communication between the memory device and the specimen handling system. The cassette may include two separable portions which can be separately distributed for processing of sorted specimens therein.

9 Claims, 6 Drawing Sheets

CASSETTE FOR USE WITH AUTOMATED SPECIMEN HANDLING SYSTEM

CROSS REFERENCE TO RELATED APPLICATIONS

The present application is related to the following applications which are filed concurrently herewith:

Automated Specimen Handling System and Method for Sorting the Specimens Filed by: Richard A. Domanik, Peter G. Gombrich, Dennis W. Gruber, and William J. Mayer Cytological Specimen Analysis System with Individualized Patient Data Filed by: Vladimir Dadeshidze, Richard A. Domanik, Peter G. Gombrich and Lars Jonas Olsson Three Dimension Mouse Filed by: Richard A. Domanik, Peter G. Gombrich, Dennis W. Gruber, Gordon Guth, and William J. Mayer System for Simplifying the Implementation of Specified Functions Filed by: Richard A. Domanik, Dennis W. Gruber, and William J. Mayer Multifunctional Control Unit for a Microscope Filed by: Richard A. Domanik, Dennis W. Gruber, Peter G. Gombrich, and William J. Mayer Specimen Management System Filed by: Richard A. Domanik, Peter G. Gombrich, and William J. Mayer Each of the above applications is assigned to the assignee of the present application and is hereby incorporated by reference.

FIELD OF THE INVENTION

The present invention is directed generally to the field of analyzing specimens, e.g., biological specimens, to detect the presence of abnormalities in the specimens, and the handling and sorting of the specimens. More specifically, the present invention is directed to a specimen transporting cassette for use with an automated specimen handling system which incorporates a memory device coupled thereto.

BACKGROUND OF THE INVENTION

Analysis of specimens, specifically biological specimens in laboratories, typically requires a technician to analyze an overwhelming amount of specimens in a short period of time. Indeed, lab technicians have been known to examine more than 40,000 slides annually in attempting to diagnose cancer from Pap smear specimens. In many laboratories, requirements for lab technicians to review excessive quantities of specimens are driven in part to the laboratories being compensated based on the number of specimens analyzed. Further, many laboratories utilize primarily manual systems for analyzing, handling, and sorting the specimens. This combination of overworked technicians and requiring the technicians to perform numerous manual tasks is a recipe for a high amount of diagnostic and inventory errors. These errors are extremely costly to individuals who have been misdiagnosed due to these errors, and to society at large.

In typical cytologic practice, groups of up to twenty specimens are distributed to the cytotechnologists for screening. Based upon the results of the screening process, the cytotechnologist divides these specimens into multiple classifications including, but not limited to, negative and positive for further processing. Depending upon the established practices of the particular laboratory, other common classifications can include high risk specimens and multiple gradations of apparent abnormality. Specimens classified as being negative are typically processed and reported using different procedures than are applied to the other categories. Similarly, high risk specimens are often subjected to different review procedures than positive specimens, which may be evaluated differently depending up the apparent degree or type of abnormality. In other words, the classification assigned by the cytotechnologist and the practices of the particular laboratory determines subsequent distribution and processing of each specimen. The sorting and distribution of screened specimens is traditionally performed manually by the cytotechnologists whether the screening is performed manually, on a motorized microscope or by an automated screening system.

Numerous attempts have been made to improve the efficiency of the specimen handling process by the introduction of various degrees of mechanization and automation. A typical system of this type consists of a cassette to store the specimens and to present them to a robotics slide handler that transfers individual specimens to the microscope for screening. These systems typically return screened specimens to their original locations in the cassette after classification. However, some systems will deliver screened specimen to another cassette. Final sorting and distribution of these specimens is accomplished by the traditional manual methods.

Accordingly, a cassette for use with an automated specimen handling system was thus needed which would enhance the efficiency of the automated specimen handling system.

SUMMARY OF THE INVENTION

It is a principle object of the present invention to provide a cassette for use with an automated specimen handling system which enhances the efficiency of the automated specimen handling system.

It is another object of the invention to provide a cassette which electronically interfaces with an automated specimen handling system.

It is yet another object of the invention to provide a cassette with a memory element containing data associated with the slides located in the cassette, such that the slides in the cassette can be automatically sorted when the cassette is removed from its automated specimen handling system.

These and other objects are achieved by the present invention which, according to one aspect, provides a portable cassette for use with an automated specimen handling system. The cassette includes a body portion, an electronic programmable memory device attached to the body portion, and an electrical conductor coupled to the memory device. The body portion includes right and left opposing sidewalls, and a substantially open front face between the opposing sidewalls. A plurality of ribs compartmentalize the body portion into superimposed sections, each capable of containing a specimen. The substantially open front face permits the specimens to be inserted into and withdrawn from the cassette. The electrical conductor interfaces with the specimen handling system and permits communication between the memory device and the specimen handling system.

In another aspect, the invention provides a portable cassette for use with an automated specimen handling system. The cassette includes a first portion and a second portion which are vertically superimposed and separable from one another permitting independent distribution of the portions. The first portion includes right and left opposing sidewalls, and a substantially open front face between the opposing sidewalls. A plurality of fibs compartmentalize the first portion into superimposed sections, each capable of containing a specimen. The substantially open front face permits specimens to be inserted into and withdrawn from the first portion of the cassette. The second portion includes right and left opposing sidewalls, and a substantially open front face between the opposing sidewalls. The second portion being capable of containing a plurality of specimens, and the substantially open front face permits the specimens to be inserted into and withdrawn from the second portion of the cassette.

These and other features and advantages of the present invention may be better understood by considering the following detailed description of certain preferred embodiments of the invention. In the course of this description, reference will be made to the attached drawings.

BRIEF DESCRIPTION OF THE DRAWINGS

Various objects, features, and attendant advantages of the present invention can be more fully appreciated as the same become better understood with reference to the following detailed description of the present invention when considered in connection with the accompanying drawings, in which.

DETAILED DESCRIPTION OF THE PREFERRED EMBODIMENT

Figure 1:
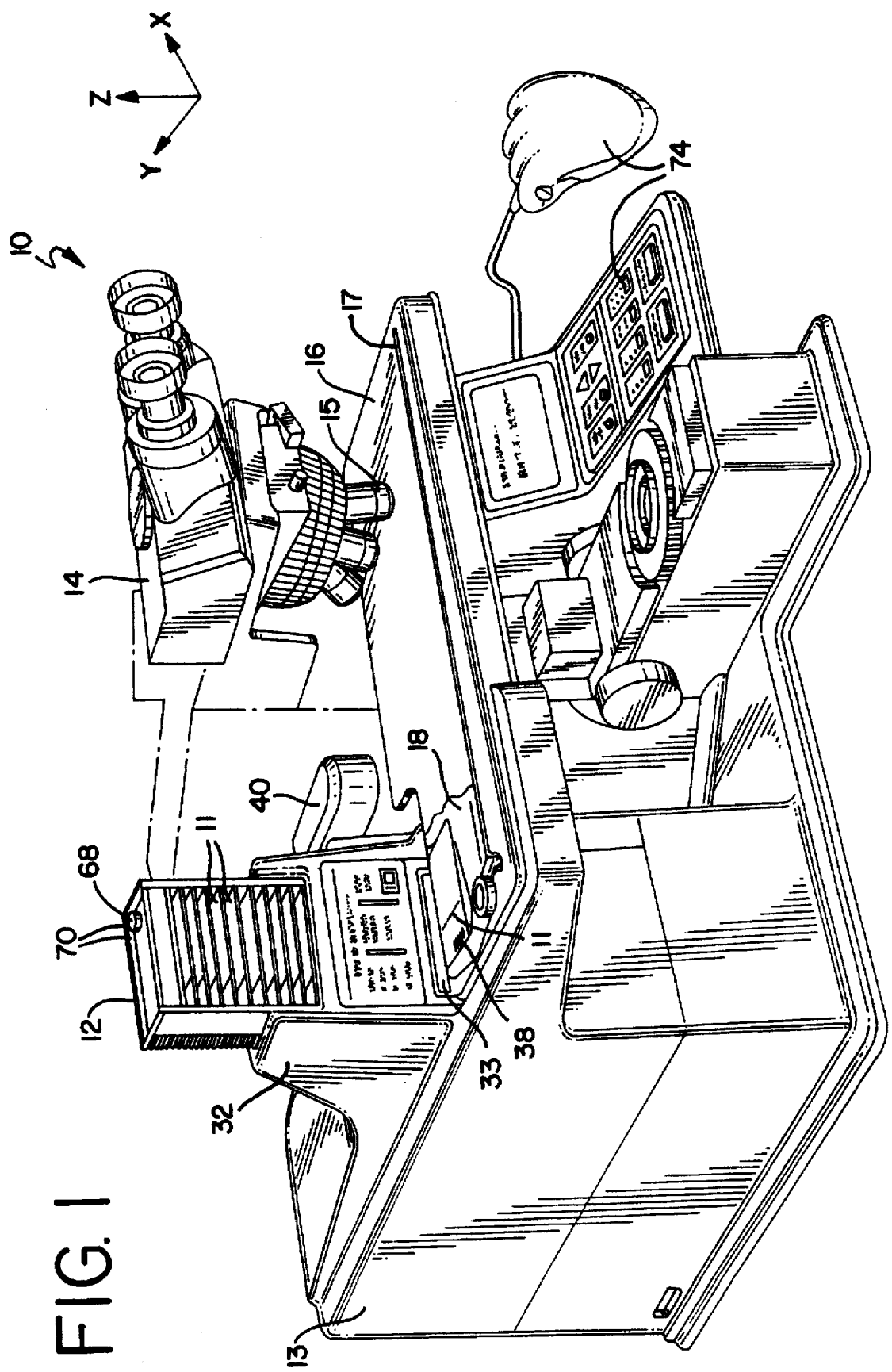
FIG. 1 is a perspective view of an automated specimen handling system using the cassette according to the present invention.

FIGS. 1-8 of the drawings illustrate an automated specimen handling system 10 in which slides 11 are delivered in a cassette 12, and are individually transported to a microscope 14 for inspection, testing, and categorization. It should be noted that while the present invention is specifically described herein for an integrated system intended primarily for the handling and screening of Pap smear specimens on slides, it is recognized that the present invention need not be limited as such and can be used or adapted to inspect and handle other specimens on other medium.

The automated specimen handling system 10 includes a microscope 14 having one or more lenses 15, and a slide handling system for transporting the slides 11 between the cassette 12 and the microscope 14. Preferably, the microscope 14 is an automated computer controlled motorized video microscope based upon a frame 13. Such a microscope and frame is commercially available from the Olympus Optical Corporation of Tokyo, Japan.

Figure 2:
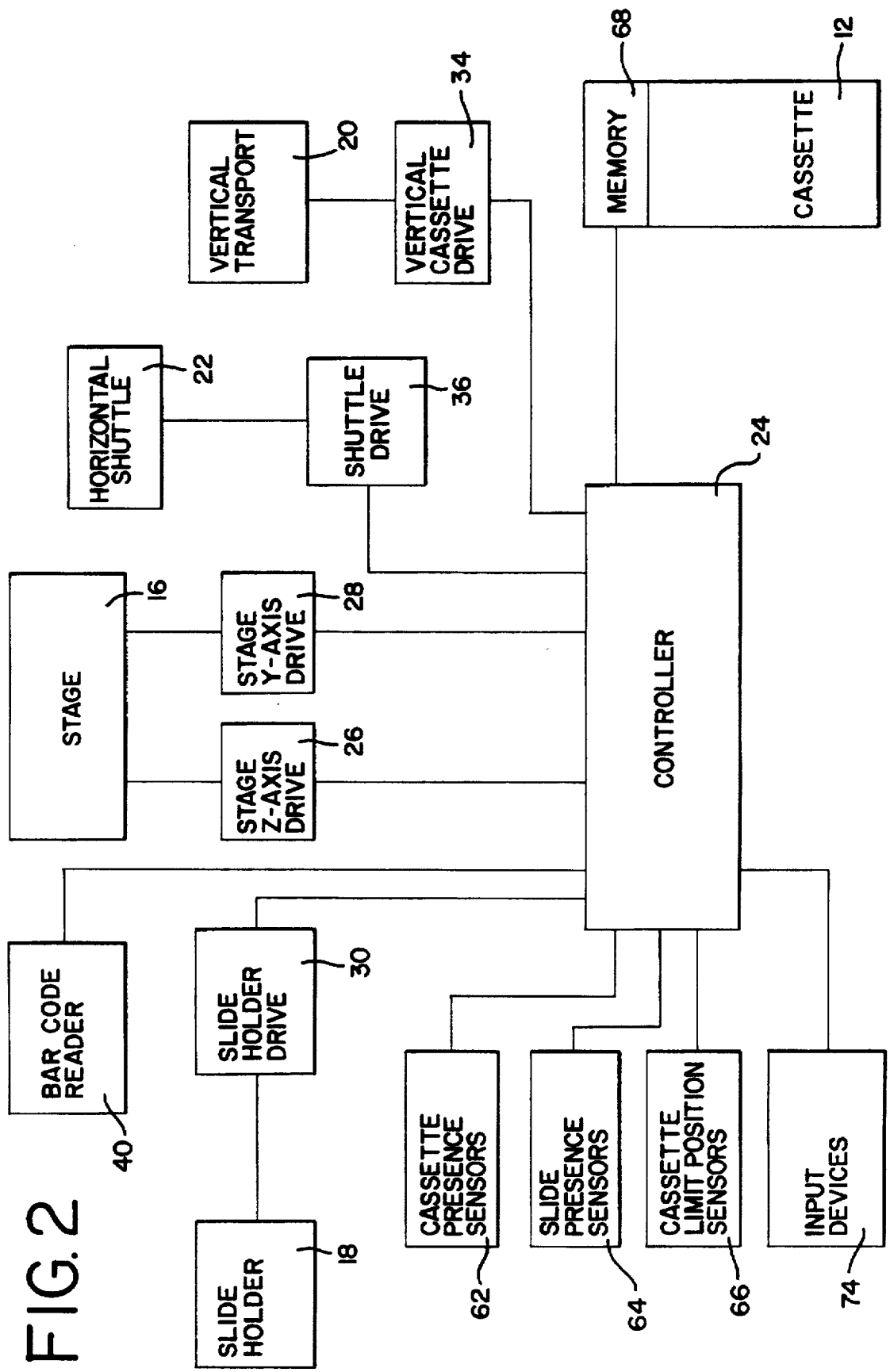
FIG. 2 is schematic block diagram of the cassette and the automated specimen handling system of FIG. 1.

The slide handling system includes a motorized stage 16, a slide holder 18 which is movable along the stage 16, a vertical transport 20 for vertically moving the cassette 12, and a horizontal shuttle 22 for moving slides between the cassette 12 and the slide holder 18. Further, as depicted in FIG. 2, a controller 24 is coupled to these elements 16, 18, 20, and 22, via respective drives, to move these elements is their desired directions.

The movable stage 16 is coupled to the frame 13 for movement along the Z-axis and along the Y-axis, by respective drives 26 and 28. The slide handler 18 is mounted for slidable movement along the X-axis with respect to the stage 16 between the microscope lens 14 and the region adjacent the cassette 12, and is driven for movement in that axis by the slide holder drive 30. Thus, movement of the stage 16 and the slide holder 18 allows a slide 11 in the slide holder 18 to move in two-dimensions relative to a lens 15 on the microscope 14. In a preferred embodiment, these drives 26, 28, and 30 may be screw drives. However, it is recognized that other drive arrangements could also effectively be used. For alignment and space efficiency purposes, it is preferable that a lower portion, not shown, of the slide handler 18 extends through a slot 17 in the stage 16. This permits the slide handler 18 to be driven from beneath the stage 16.

The cassettes 12 are portable and can be transported to and from the system 10. The cassettes 12 are deposited inside a casing 32 which houses the vertical transport 20 and the horizontal shuttle 22. The vertical transport 20 is mounted for movement along the Z-axis with respect to the frame 13, and is driven for movement in that axis by a vertical cassette drive 34. The horizontal shuttle 22 is mounted for movement along the Y-axis with respect to the frame 13, and is driven for movement in that axis by a shuttle drive 36. In a preferred embodiment, these drives 34 and 36 may be gear and rack drives. However, it is recognized that other drive arrangements could also effectively be used.

The relative movement in the Z-axis between the horizontal shuttle 22 and the vertical transport 20, caused by the vertical cassette drive 34, permits the shuttle 22 to remove and deposit slides 11 into predetermined locations in the cassette 12. The movement of the horizontal shuttle 22 in the Y-axis caused by shuttle drive 36 permits the shuttle 22 to move the slides 11 between the cassette region and the slide holder region. The relative movement in the Z-axis between the horizontal shuttle 22 and the slide holder 18, caused by the vertical stage drive 28, permits the shuttle 22 to remove and deposit slides 11 onto the slide handler 18.

The slides 11 include a identifying indicia thereon which preferably takes the form of a barcode 38. A barcode reader 40 is located between the cassette 12 and the microscope 14 so that the identifier on each slide 11 is read as is it transported between the cassette 12 and the microscope 14. Further, the barcode reader 40 may also be adapted to write onto the slides 11 to provide additional data for processing. Details directed to the system for utilizing the barcode and reader are disclosed in the aforementioned patent applications which have been incorporated herein by reference. Thus, the system 10 incorporates a cassette based specimen handling system with integral barcode reading capability.

It should be noted that the controller 24 can take the form of any control circuitry, and is preferably programmed to include various memory devices and be preprogrammed to execute various standard sorting procedures.

Details of the cassette 12 and its interface with the vertical transport 20 and horizontal shuttle 22 of the automated specimen handling system 10 are now described in conjunction with FIGS. 1-5. Cassette 12 includes a body portion 42 defined by right and left opposing side walls 44 and 46, top and bottom walls 48 and 50, and front and rear faces 52 and 54 which are substantially open to permit the entry and exit slides 11 and also to permit the horizontal shuttle 22 to pass therethrough.

The interior surfaces of the side walls 44 and 46 include a plurality of ribs 56 to compartmentalize the cassette 12 so that it can house and transport up to forty slides 11. Preferably, the ribs 56 have a trapezoidal type profile to contact the slides 11 at two separated points as opposed to a continuous surface.

Figure 3:
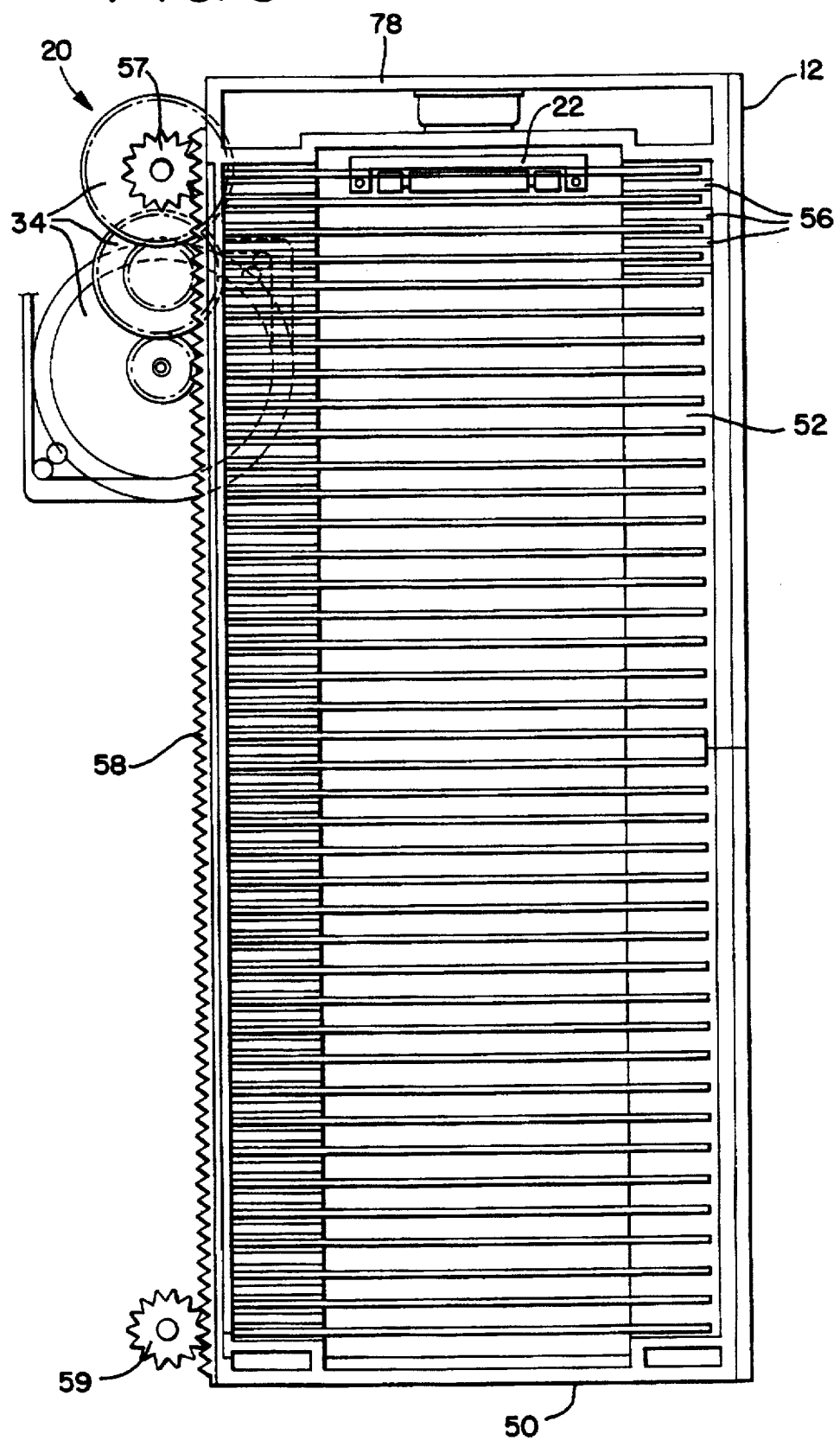
FIGS. 3-5 are front elevational, right side elevational, and top plan views of the cassette and its interface with the vertical transport and horizontal shuttle of the automated specimen handling system of FIG. 1.
Figure 4:
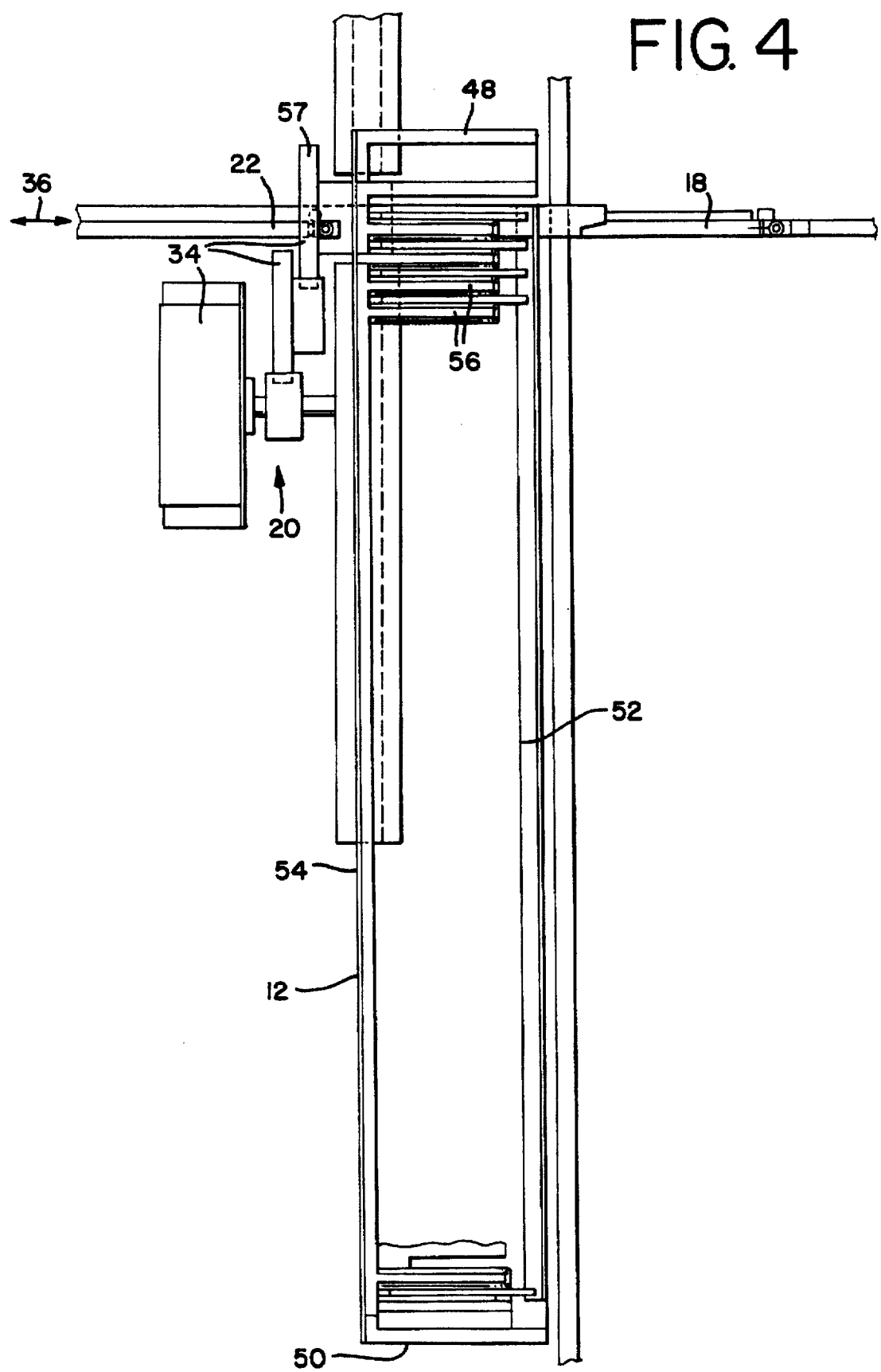
Figure 5:
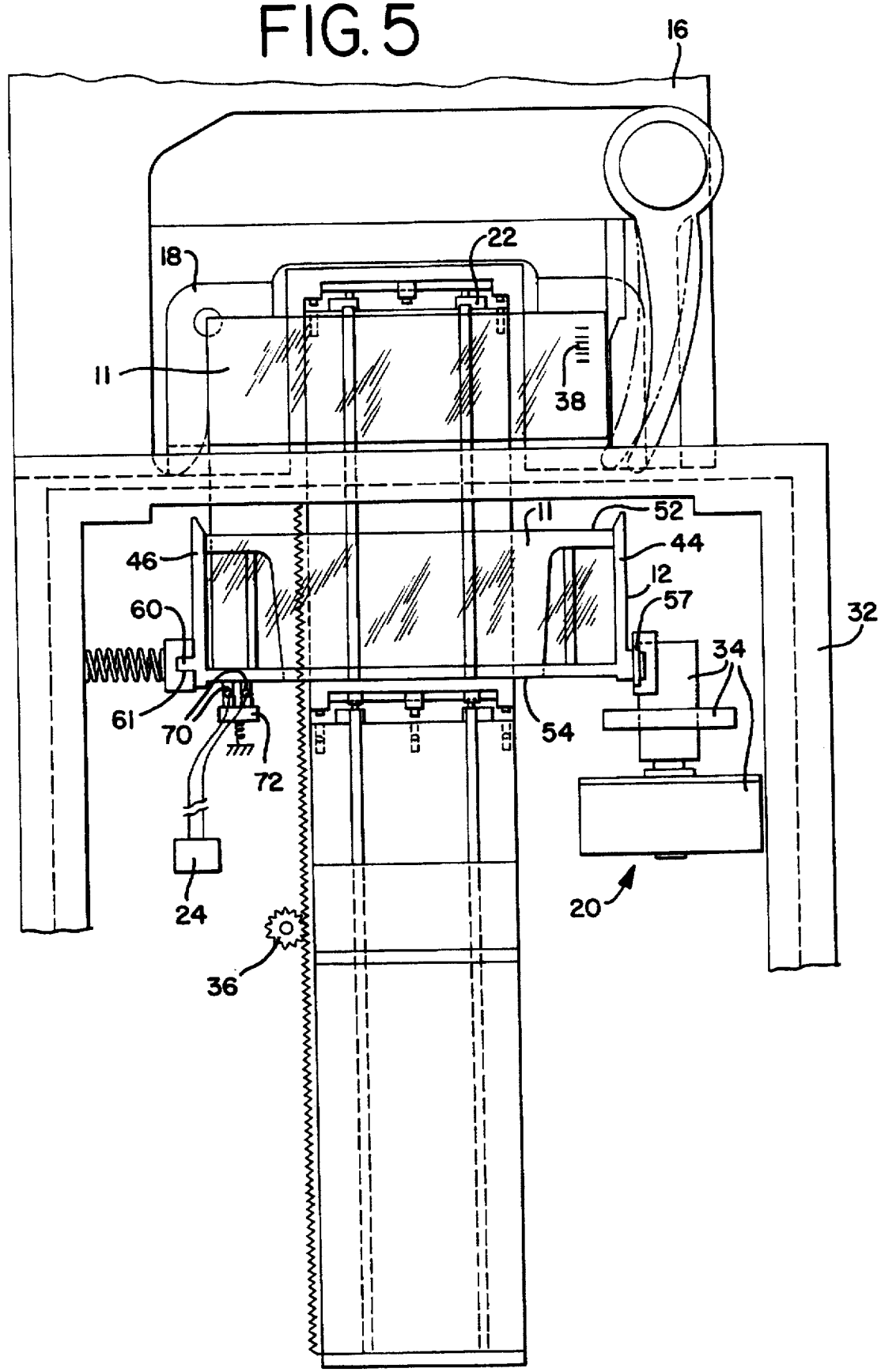

As seen in FIGS. 3–5, the cassette 12 also includes a gear rack 58 molded into the cassette 12. The gear rack 58 mates with one driven 57 and at least one idler gear 59, which form part of the vertical cassette drive 34, to provide cassette positioning in the vertical direction. Further, a guide projection 60 is molded into the cassette 12 on the exterior surface on the side wall 46 which opposite the gear rack 58. This mates with a biased guide slot member 61 to help guide the cassette 12 in its vertical motion. Further, additional guide rails are molded into the cassette 12 which mate with corresponding features in the elevator walls to guide the cassette motion during the loading of the cassette 12 into the elevator/vertical transport 20 and during normal vertical movement. It should be noted that, cassette presence sensors 62, slide presence sensors 64, and cassette limit position sensors 66 are positioned in or adjacent the elevator/vertical transport 20. These sensors 62, 64, and 66 communicate with the controller 24 and provide status feedback.

The cassette 12 also includes an electronic memory device 68 attached thereto. A pair of electrically conductive bus bars 70 extend vertically along an external wall surface of the cassette 12 to electrically couple to the memory device 68 to the controller 24 and facilitate the sorting and handling of the slides 11. As described hereinafter, the memory device 68 permits the cassette 12 to be removed from the vertical transport 20, and sorted at an external location. In a preferred embodiment, the bar bars 70 interface with a biased connector 72 to assure proper connection between the memory device 68 and the controller 24, regardless of the vertical position of the cassette 12. If desired, one or more metallic inserts, not shown, may be folded around the molded body portion of the cassette 12 to provide both the bus bar surfaces 70 and the ribs 56.

The memory device 68 is preferably a serial EEPROM memory device, i.e., an electronically erasable programmable read only memory chip that holds its content without power. Such a device is commercially available and manufactured by Dallas Semiconductor. The memory device 68 would preferably be housed in a button package, not shown, and configured for a two wire interface.

Additionally, controller 24 is coupled to one or more input devices 74 which can be buttons on a control panel or a movable mouse. This provides the user of the microscope system the capability to manually pause and restart the automatic sequences, or to insert or remove slides 11 from the automatic processing by entering appropriate commands on the input devices 24.

In operation, a slide 11 is transferred from the cassette 12 to the microscope 14. To accomplish this the vertical cassette drive 34 vertically positions the cassette 12 so that the desired slide 11 is adjacent a port 33 in the casing 32. The shuttle drive 36 then moves the horizontal shuttle 22 along the Y-axis towards the slide holder 18, stopping when the shuttle 22 is positioned immediately below the slide 11 to be transferred. The vertical cassette drive 34 lowers the cassette 12 until the slide 11 rests on the horizontal shuttle 22. The shuttle drive 36 moves the horizontal shuttle 22, with the slide 11 thereon, along the Y-axis towards the slide holder 18, stopping when the shuttle 22 is positioned immediately above the slide holder 18. The vertical stage driver 26 raises the stage 16 until the slide 11 rests on the slide holder 18. The slide holder drive 30 moves the slider holder 18 to the desired position under the microscope lens 15. It should be noted, however, that during the travel of the slide holder 18 from the cassette region to the microscope lens region, the indicia 38 from the slide 11, is read by the bar code reader 40. This indicia 38 is conveyed to the controller 24 along with other information carded by the slide 11.

The specimen on the slide 11 is examined and categorized, with none, some, or all of this procedure being done automatically. The slide 11 is then returned to a desired position in the cassette 12 by performing the aforementioned steps in reverse order. Optionally, the indicia 38 on the slide 11 is confirmed by the bar code reader 40. The slide indicia 38, its assigned category, and its placement in the cassette 12 are stored in the memory device 68.

The system can sort the slides 11 in the cassette 12 in a number of different ways. One method is by programming the memory device 68 to include all data necessary for sorting the contents of the cassette 12 at a remote location. Preferably, the first step is to erase all information from the memory device 68 except for a cassette identification code. As each slide 11 is transferred from the cassette 12 to the microscope 14 the reader 40 determines the identity of the specimen that was loaded. Further, the number of the slot in the cassette from which it was extracted can be determined by the controller 24 by the cassette position sensor 66 or any other positional feedback sensor. Upon completion of screening, the classification of the specimen is available to the controller 24 and the memory device 68. Similarly, the cassette slot to which a specimen is returned, or the diversion of a specimen for manual unloading, is also known to the controller 24. Thus, the source, the identity, the classification, and the destination of for each slide 11 can be recorded in the cassette memory 68. When the cassette 12 is removed from the slide handling system 10, its memory device 68 contains a complete and accurate summary of the contents of each slot. This information can be accessed at a separate station for sorting the specimens for subsequent routing and for generating process statistics.

Additionally, sorting of the slides 11 in the cassette 12 can be done by classification using the slide handling system 10. This can be done either (i) as the slides 11 are being returned to the cassette 12 after screening or (ii) as a separate operation after screening is completed, but before the cassette 12 is removed from the system. If it is desired to sort the slides 11 as they are being returned to the cassette 12, the specimens could be loaded in the first ten slots of a twenty slot cassette. Assume also that these ten specimens are to be sorted into three different categories: negative, high risk and positive. From experience and under normal circumstances, it can be presumed that less than 10% of the specimens can be anticipated to be positive and less than 40% high risk. This permits the first ten slots to be dedicated to the negative specimens, the next six slots to be dedicated to high risk specimens, and the remaining four slots to be dedicated to positive specimens. As the specimens are being returned to the cassette 12 after screening, they are returned to the first available slot in the subsection corresponding to their classification. The destination field of the cassette memory device 68 is updated accordingly.

Batch sorting requires at least one open cassette slot or the ability to temporarily leave at least one slide 11 on the stage or at another location. Once all of the slides 11 in the cassette 12 have been screened, their classifications and locations are known and the appropriate number of slots can be allocated to each category by the controller 24. If, for example, of the nineteen specimens in a twenty slot cassette, ten were negative specimens, two were positive specimens, and seven were high risk specimens, the controller 24 could assign slots one through ten to negative specimens, slots eleven and twelve to positive specimens, and slots thirteen through nineteen to high risk specimens. One possible sorting sequence would be to examine the classification of each specimen in order of increasing slot number until the first non-negative specimen was located. This specimen would be moved to slot 20 and parked. This opens a slot in the negative section of the cassette. Examination of the classifications then continues with the first slot assigned to the same classification as the specimen parked in slot 20 until the first negative specimen in this section is found. This negative specimen is moved to the open slot in the negative section and the specimen parked in slot 20 is moved to the slot just vacated in its section. This cycle is then repeated until all slides are in their appropriate section. However, it is apparent that other sorting techniques could be used. Regardless of the specific sorting technique used, the cassette memory 86 is then updated to reflect the sorted specimen locations. The cassette 12 is then ejected from the system, and a new cassette 12 is loaded.

Figure 6:
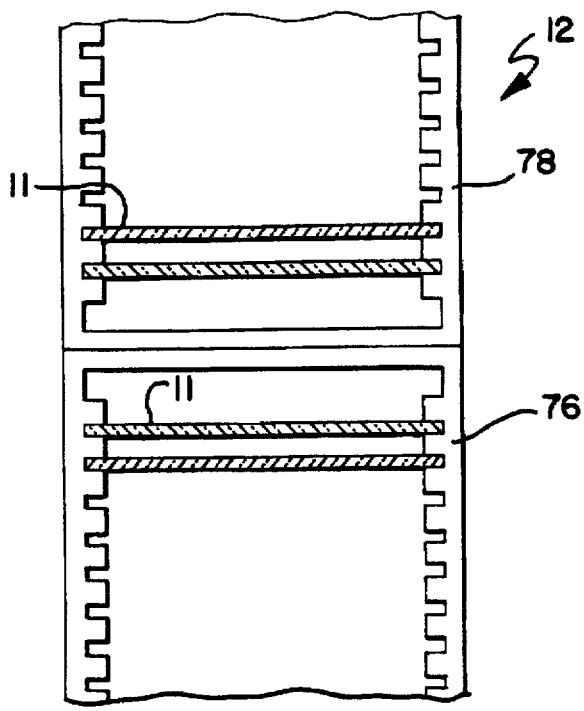
FIG. 6 is a front elevational view of a first cassette embodiment having detachable sections.
Figure 7:
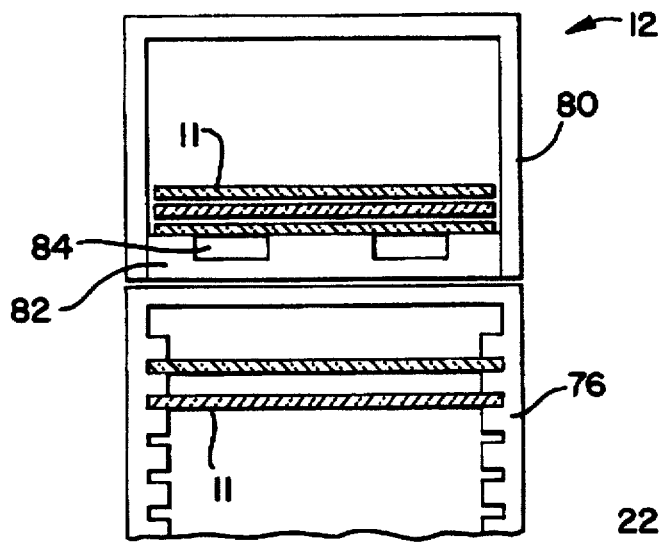
FIG. 7 is a front elevational view of a second cassette embodiment having detachable sections.
Figure 8:
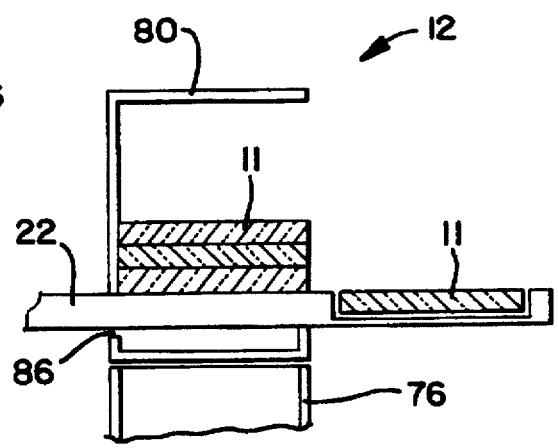
FIG. 8 is a side elevational view of cassette embodiment of FIG. 7.

The efficiency relating to sorting specimens within a cassette is further enhanced by the cassette designs shown in FIGS. 6–8. The cassette designs in FIGS. 6–8 include two or more sections such that the sorted slides can be distributed without being removed from the cassette 12. Preferably, the cassette sections 76 and 78 or 80 link, snap, slide, or are otherwise removably attached to each other so that they form a larger cassette 12 when attached. In the embodiment shown in FIGS. 6, both the upper section 78 and the lower section 76 include ribs for holding the slides, as described supra. In another cassette design, not shown, the cassette includes a frame into which multiple slide carriers can be inserted.

In the embodiment shown in FIGS. 7 and 8, ribs are utilized in the lower section 76. However, no ribs are required in the upper section 80 and the slides 11 can be stacked directly upon one another in the upper section 80. In lieu of ribs, the upper section 80 includes a floor 82 which supports a stack of slides 11. The floor 82 includes recesses 84 therein to permit passage of the horizontal shuttle 22. To load a slide 11 into the upper section 80, the shuttle 22 is extended through the recesses 84 to the stage 16. The stage 16 is lowered to place the slide 11 in the shuttle 22. The cassette 12 is then lowered such that the stack of slides 11 rests on the shuttle arm 22. The shuttle 22 is retracted and becomes the lowermost slide in the stack. Lastly, the cassette 12 can be raised, and the shuttle 22 can be fully retracted.

In any of the split cassette designs, the slides to be screened would be placed into one section with the non-negative specimens being sorted into other originally empty sections or carriers according to their classifications. The negative specimens would be returned to their original sections, although not necessarily to their original slots. Upon completion of the screening, the sections would be separated or the inserts removed form the carrier and distributed in the appropriate manner as units. If desired, memory devices can be used in one or more sections in the split cassettes.

Another advantage achieved by the present invention is that the cassette memory 68 can be used to record the identity of the specimen in each slot before loading the cassette 12 into the slide handling system. By reading the stored identification information, the controller 24 can access and display the corresponding patient information to assist the operator during the screening process. One limitation to this approach is that it is possible to inadvertently insert a specimen into a slot other than the one programmed or to insert the wrong specimen into a designate slot. However, the bar code reader 40 would confirm the identification of each specimen loaded onto the stage and inform the operator of any discrepancies.

A preferred embodiment of the present invention has been described herein. It is to be understood, of course, that changes and modifications may be made in the embodiment without departing from the true scope and spirit of the present invention, as defined by the appended claims.

We claim:

1. A portable cassette for use with an automated specimen handling system, said cassette comprising:

a body portion, said body portion including right and left opposing sidewalls, a front face between the opposing sidewalls, and a plurality of ribs compartmentalizing the body portion into superimposed sections, each section capable of containing a specimen, said front face being substantially open permitting the specimens to be inserted into and withdrawn from the cassette;

an electronic programmable memory device attached to the body portion;

at least one electrically conductive member physically coupled to the memory device for interfacing with the specimen handling system and for permitting communication between the memory device and the specimen handling system.

2. The cassette of claim 1, wherein said body portion includes a plurality of external surfaces, said electrically conductive member extending vertically along one of said plurality of external surfaces.

3. The cassette of claim 1, wherein said at least one electrically conductive member includes a pair of electrically conductive members for interfacing with the specimen handling system and for permitting communication between the memory device and the specimen handling system, each said electrically conductive member including a bus bar.

4. The cassette of claim 1, wherein said memory device includes means for storing information regarding the specimens contained in the cassette.

5. The cassette of claim 4, wherein said information includes an identifier for each specimen and the relative position of each specimen within the cassette.

6. The cassette of claim 5, wherein said information further includes a classification for each specimen within the cassette.

7. The cassette of claim 1, wherein said electronic programmable memory device includes a memory chip that holds its content in the absence of power.

8. The cassette of claim 1, further comprising a portable power supply attached to said body portion and coupled to said memory device for providing power to said memory device.

9. The cassette of claim 1, wherein said cassette includes first and second portion removably coupled to one another, wherein each said first and second portion includes right and left opposing sidewalls, a front face between the opposing sidewalls, and a plurality of ribs compartmentalizing the body portion into superimposed sections, each section capable of containing a specimen, said front face being substantially open permitting the specimens to be inserted into and withdrawn from the cassette, said first and second portions being vertically superimposed.

* * * * *